US 6,712,850 B2

(12) United States Patent
Vyakarnam et al.

(10) Patent No.: US 6,712,850 B2
(45) Date of Patent: Mar. 30, 2004

(54) POROUS TISSUE SCAFFOLDS FOR THE REPAIR AND REGENERATION OF DERMAL TISSUE

(75) Inventors: Murty Narayan Vyakarnam, New York, NY (US); Mark Charles Zimmerman, East Brunswick, NJ (US); Anna Gosiewska, Skillman, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/016,808

(22) Filed: Nov. 30, 2001

(65) Prior Publication Data

US 2003/0105525 A1 Jun. 5, 2003

(51) Int. Cl.[7] .................................................. A61F 2/10
(52) U.S. Cl. .................... 623/15.12; 623/924; 623/925; 623/926; 623/11.11; 623/66.1
(58) Field of Search ................ 424/422–426; 623/924–926, 11.11, 66.1, 15.11–15.12, 23.72, 23.75–23.76; 523/113–114; 606/230

(56) References Cited

U.S. PATENT DOCUMENTS

| 4,186,448 | A | | 2/1980 | Brekke |
| 5,133,755 | A | | 7/1992 | Brekke |
| 5,468,253 | A | | 11/1995 | Bezwada |
| 5,514,378 | A | | 5/1996 | Mikos et al. |
| 5,522,895 | A | | 6/1996 | Mikos |
| 5,607,474 | A | | 3/1997 | Athanasiou et al. |
| 5,677,355 | A | | 10/1997 | Shalaby |
| 5,686,091 | A | | 11/1997 | Leong et al. |
| 5,711,960 | A | | 1/1998 | Shikinami |
| 5,716,413 | A | | 2/1998 | Walter et al. |
| 5,755,792 | A | | 5/1998 | Brekke |
| 5,769,899 | A | | 6/1998 | Schwartz et al. |
| 5,770,193 | A | | 6/1998 | Vacanti et al. |
| 6,333,029 | B1 | * | 12/2001 | Vyakarnam et al. ....... 424/93.1 |
| 2003/0004578 | A1 | * | 1/2003 | Brown et al. ............ 623/23.72 |

FOREIGN PATENT DOCUMENTS

| EP | 02 74898 A2 | 7/1988 |
| EP | 0 714 666 A | 6/1996 |
| WO | WO 01 02033 A | 1/2001 |

OTHER PUBLICATIONS

Kwon, I.K. et al; "Fibroblast culture on surface–modified poly(glycolide–co–epsilon–cparolactone"; J. Biomater. Sci. Polymer EDN.; 2001; pp. 1147–1160; vol. 12, No. 10.

* cited by examiner

*Primary Examiner*—David J. Isabella
*Assistant Examiner*—Urmi Chattopadhyay

(57) ABSTRACT

The present invention is a synthetic, biocompatible, bioabsorbable, porous foam tissue scaffolds possessing physicochemical properties suitable for use in the repair and regeneration of dermal tissue and to methods of preparing the foam scaffold.

10 Claims, 2 Drawing Sheets

75 μm

75 μm

75 μm

100 μm

100 μm

100 μm

POROUS TISSUE SCAFFOLDS FOR THE REPAIR AND REGENERATION OF DERMAL TISSUE

FIELD OF THE INVENTION

This invention relates to synthetic, bioabsorbable, porous foam tissue scaffolds and to the repair and regeneration of dermal tissue.

BACKGROUND OF THE INVENTION

There is a growing demand for foams for biomedical applications such as scaffolds for tissue engineering, wound healing dressing and other implantable wound healing, augmentation, and regeneration devices. Specifically these foams have been made from biocompatible polymers and have an open celled microstructure.

Open cell porous biocompatible foams have been recognized to have significant potential for use in the repair and regeneration of tissue. Early efforts in tissue repair focused on the use of biocompatible foam as porous plugs to fill voids in bone.

Several attempts have been made in the recent past to make tissue engineering scaffolds using different methods for dermal tissue. Animal derived materials are known for use as acellular scaffolds used in regeneration of skin. However, most approaches using biodegradable synthetic scaffolds or animal derived materials have involved cell expansion and seeding onto the scaffolds, resulting in an in-vitro cultured substitute for skin. These products have had mixed clinical success and are far from optimum. Such approaches have one or more drawbacks from a viable product standpoint in the way of, for example, limited shelf life, difficulty in handling and storage, and expense due to the difficult cell culturing process. Lyophilization lends itself to many advantages when processing thermally sensitive polymers. Further, it lends itself to aseptic processing methodologies for bio-medical applications, especially when using combinations of polymers with drugs or other bioactive agents such as growth factors, proteins etc.

While improved processes for making foams generally useful as scaffolds for tissue engineering are known, which processes utilize lyophilization under certain identified conditions, it would be advantageous to provide a lyophilization process for providing foams that are particularly well suited for use as tissue scaffolds in the repair and regeneration of dermal tissue, e.g. skin, and to provide foams having physicochemical properties suitable for use in the repair and regeneration of dermal tissue.

SUMMARY OF THE INVENTION

The present invention is directed to synthetic, biocompatible, bioabsorbable foam tissue scaffolds comprising physicochemical properties suitable for use in the repair and/or regeneration of dermal tissue and to methods of preparing such foams, which methods comprise preparing a homogenous solution comprising a synthetic, biocompatible, bioabsorbable, aliphatic, elastomeric copolymer comprising copolymerized $\epsilon$-caprolactone and glycolide at a molar ratio of $\epsilon$-caprolactone:glycolide ranging from about 30:70 to about 40:60 and a solvent in which the copolymer is soluble, wherein the homogenous solution comprises from about 4 to about 6 weight percent, and preferably about 5 weight percent, of the copolymer and about 95 percent by weight of the solvent, placing an effective volume of the homogenous solution in a mold or other device suitable for preparing foam tissue scaffolds suitable for use in repair and regeneration of dermal tissue, quenching the homogenous solution at a temperature and at a rate sufficient to provide foam tissue scaffolds suitable for use in repair and regeneration of dermal tissue, solidifying the solution to form a solid and removing the solvent from the solid to provide a biocompatible, bioabsorbable porous foam suitable for use in the repair and regeneration of dermal tissue.

DETAILED DESCRIPTION OF THE INVENTION

Figure 1A:
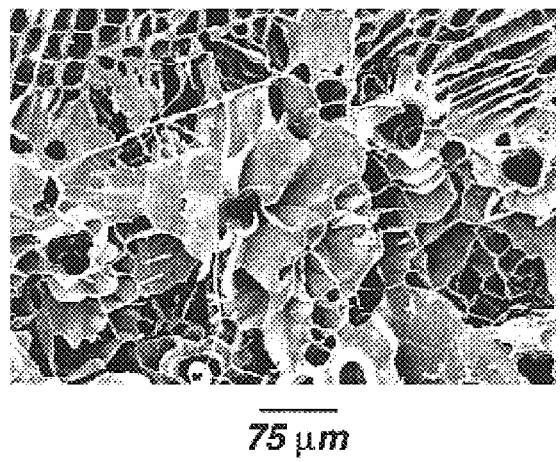
FIG. 1a is a scanning electron micrograph of the top surface of a foam scaffold according to the present invention.

Foams according to the present invention are particularly useful as tissue scaffolds in the acellular repair and regeneration of dermal tissue, i.e. skin. Acellular repair and regeneration of dermal tissue does not require seeding of cells onto scaffolds or otherwise culturing cells on scaffolds prior to implantation into a patient.

Skin is a layered organ of which dermis may be regarded as the primary structure. It is overlaid by epidermis and underlaid by hypodermis. The basic structure of the skin tissue when it comes to repair and regeneration has two distinct, but well integrated, layers, e.g. the epidermis and dermis, where the thickness of each layer varies at different locations of the body. The epidermis, which typically is very thin, e.g. 40–80 microns, excepting in places like the palm and fingertip, consists of up to five layers, depending on the region of the body. While the superficial layer, i.e. stratum corneum, could be hard and sometimes horny, the deepest layer, i.e. stratum germinativum, is composed of soft protoplasmic columnar cells, many in mitosis. The dermis has a papillary and a reticular layer. The papillary layer is adjacent to the basement membrane of the epidermis and includes ridges and papillae of fine connective tissue fibers. The reticular layer is the main fibrous bed of the dermis, consisting of thick, coarse, densely interlacing, collagenous fibers parallel to the surface. The dermis merges with the underlying sub-cutaneous layer, which is the hypodermis layer. The hypodermis is not regarded as part of skin and is composed mainly of an adipose layer.

The outer layer, or epidermis, is a vascular and mainly consists of keratinocytes, with smaller numbers of immune cells (Langerhan cells) and pigmented cells (melanocytes). The keratinocytes produce keratin fibers and corneocyte envelopes, which gives the epidermis its durability and protective capabilities. The development of these structures is dependent completely upon the differentiation state of the epidermis. The epidermis forms a stratified epithelium, with different protein expression patterns as the cells move further away from the basement membrane. This stratified layer of differentially expressing cells must be formed for maintenance of epidermal function.

Below the epidermis is the dermis, which is a dense irregular connective tissue that is highly vascular. This layer is populated heavily with collageneic and elastic fibers, which give it its exceptional elasticity and strength. Fibroblasts are the main cell types in this layer. Between these two layers is the basement membrane, which serves as the site of attachment for epidermal cells and serves also to regulate their function and differentiation. The layer of keratinocytes, which attaches directly to the basement membrane, are cuboidal in shape and highly aligned. This attachment and architecture are critical requirements driving the ultimate production of the higher squamous structures in the epidermis. The basal layer provides a source of precursor cells for repair and replacement of the epidermis. The squamous layers provide strength and resistance to insult and infection.

Many leg ulcers still have remnants of epidermal appendages in the wound bed from which re-epithelialisation can occur. Using dispersions of autologous keratinocytes, it has been demonstrated previously that keratinocytes can migrate through dermal scaffolds and achieve the correct orientation. We also have demonstrated that keratinocytes can migrate through the scaffolds and may be able to contribute to the process of re-epithelialisation.

Chronic wounds have an imbalance of tissue formation and degradation and thus are impaired at the granulating phase of wound repair. In addition to this invention acting as a scaffold, it also may facilitate the progression of wound healing by changing the environment in the wound. Cell physiology is known to be affected by the environment, which may be affected by the scaffold in several ways, such as changing the availability of growth factors, moisture levels and physical interactions. The physical properties of a scaffold onto which cells are able to migrate may affect the cell physiology. The cells will experience a different substrate and tensile forces in the scaffold compared to the dermal matrix of the wound margins. Different substrates and mechanical forces have been demonstrated previously to affect fibroblast expression of matrix, growth factor receptors, integrins, growth factors, proteases and matrix proteins.

The foams of this invention are suitable for wound healing dressing and other implantable wound healing situations. They could be suitable to heal or repair venous stasis ulcers, diabetic foot ulcers, pressure sores, burns and other situations of dermal breachment. Further, this biomedical foam implant also can be used to heal large soft tissue defects that occur as a function of a surgical excision. Such surgical excisions can occur in plastic surgery applications, including cosmetic defects such as breast augmentation and restoration. These biomedical foams also can be used as scaffolds for soft tissue defects created by surgical procedures for removal of tumor in oncological procedures. These scaffolds also can be used for other soft tissue repair and augmentation related to trauma.

Any material used for replacement of skin must possess certain physicochemical properties suitable for use as a tissue scaffold in the repair and regeneration of dermal tissue. Such properties include appropriate morphology of the foam scaffolds, including suitable foam thickness and porosity, such that the foam scaffolds are infiltrated by and eventually enveloped by granulation tissue within an appropriate period of time for such uses. Selection of the appropriate copolymer suitable for the particular use in repair and regeneration of dermal tissue also is key in preparing foam scaffolds having the appropriate bioabsorption profiles.

It is proposed, but in no way limiting the scope of the invention, that the primary mechanism of action of the preferred embodiment is through its ability to provide a 3-D matrix of interconnecting pores, which acts as a scaffold for cell migration. The morphology of the scaffold guides cell migration and vascularization of tissues. Cells such as fibroblasts, endothelial cells and keratinocytes are able to migrate into or over the scaffold, respectively. The cells then are able to proliferate and synthesize new granulation tissue and form an epithelium. The scaffold facilitates the process of granulation tissue formation and re-epithelialisation by enabling the cells to migrate and synthesize new dermal matrix in the wound defect.

Accordingly, foam materials utilized in tissue scaffolds according to the present invention must be able to entice invasion thereof by fibroblasts or other cells necessary to produce the dermal components of the healed tissue. Additionally, the material must not inhibit, and preferably should enhance, the rate of re-epithelialization in such a fashion that a discreet, epidermal basal layer is formed. Materials that permit invasion into the scaffold by migrating keratinocytes can produce partially differentiated cells. Consequently, control of access of particular cell types and a porous design that facilitates the regeneration of the natural tissue can have functional benefits. Preferably, high quality granulation tissue will infiltrate the foam scaffold to a degree of about 50 percent of the foam thickness within about 10 days of implantation of the scaffold. More preferably, about 75 percent of the foam thickness will be infiltrated by granulation tissue within about 7 days of implantation of the scaffold. Preferably, the foam tissue scaffold will be substantially, e.g. about 90 percent or more, submerged in or enveloped by granulation tissue within about 28 days of implantation of the scaffold. Most preferably, the foam scaffold will be completely submerged in or enveloped by granulation tissue within about 28 days of implantation.

In order to be useful in repair and regeneration of dermal tissue, it is desirable to prepare foam tissue scaffolds having a thickness of from 0.25 mm to 0.75 mm. Preferably, the thickness of the foam may range of from about 0.4 mm to about 0.6 mm and, most preferably, the foam scaffold will have a thickness of about 0.5 mm. Clearly, different skin injuries, e.g. diabetic ulcers, venous stasis ulcers, decubitis ulcers, burns, etc., may require different foam thickness.

Additionally, the patient's condition may necessitate the incorporation of one or more therapeutic agents selected from the group consisting of anti-microbial agents, hemostatic agents, cytostatic and cytoxic drugs, anti-infectives, hormones, analgesics, anti-inflammatory agents, oncological pharmaceuticals, peptides, small molecules, growth factors, and anti-fungal compounds to facilitate wound healing. When used, such agents are employed in amounts effective to provide the desired therapeutic affect for which such agents are known. Once having the benefit of this disclosure, one skilled in the art will be able to ascertain readily what the particular effective amount is for a particular therapeutic agent.

Foams and tissue scaffolds according to the present invention must possess porosity suitable for repair and regeneration of dermal tissue. Such foams and scaffolds will have porosity of 90 percent or higher by volume.

Preferably, the foam will have porosity of from 90 to about 97 percent by volume, more preferably from 90 to about 95 percent by volume.

Scaffolds according to the present invention, which due to the composition is not proteolytically degraded but rather hydrolyses slowly, could remain intact for a longer period than a protein-based scaffold in the hostile environment of a chronic wound that has high levels of protease activity. The degradation rate of the copolymer is determined by the ratio of its constituent polymers, which can be changed to produce the optimal degradation rate. Preferably, the foam scaffolds of the present invention will be absorbed by the body within about 120 days after implantation of the scaffold in the body. More preferably, scaffolds of the present invention will be substantially, e.g. greater than about 90 percent, absorbed by the body within about 90 days of implantation, and even more preferably, the scaffolds will be totally absorbed by the body within about 90 days of implantation.

Particularly well suited polymers for the preparation of foams suitable for use as tissue scaffolds in the repair and regeneration of dermal tissue are synthetic, biocompatible, bioabsorbable, elastomeric, aliphatic polyester copolymers comprising polymerized glycolide (including glycolic acid) and $\epsilon$-caprolactone, which copolymers provide physicochemical properties to such foams that are necessary for use as tissue scaffolds in repair and regeneration of dermal tissue. For the purpose of this invention, an "elastomeric copolymer" is defined as a polymer which, at room temperature, can be stretched repeatedly to at least about twice its original length and which, upon immediate release of stress, will return to approximately its original length. Optionally, the copolymers may further comprise p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, and 6,6-dimethyl-1,4-dioxan-2-one.

Particularly well-suited bioabsorbable, biocompatible, elastomeric copolymers include elastomeric copolymers of $\epsilon$-caprolactone and glycolide; preferably having a mole ratio of $\epsilon$-caprolactone:glycolide of from about 30:70 to about 40:60, preferably about 35:65 mole ratio of $\epsilon$-caprolactone:glycolide. These elastomeric copolymers will have an inherent viscosity of from about 0.75 dL/g to about 4 dL/g, preferably an inherent viscosity of from about 1.0 dL/g to about 2 dL/g and most preferably an inherent viscosity of from about 1.3 dL/g to about 1.8 dL/g as determined at 25° C. in a 0.1 gram per deciliter (g/dL) solution of polymer in hexafluoroisopropanol (HFIP).

Foams according to the present invention are made by a modified-lyophilization process. Lyophilization processes are disclosed in PCT patent application WO01/02033, the contents of which are incorporated herein by reference as if set forth in its entirety. The features of such foams are controlled to suit the desired application by a modified lyophilization process that results in (1) interconnecting pores of sizes ranging from 10 to 200 microns (or greater) that provide pathways for cellular ingrowth and nutrient diffusion; (2) porosities preferably ranging from 90% or higher; and (3) channels that run through thickness of the foam for improved vascularization and nutrient diffusion. It is preferred that foams used in tissue scaffolds of the present invention have a structure that provides organization at the microstructural level that provides a template that facilitates cellular organization that mimic natural dermal tissue. The cells will adhere, proliferate and differentiate along the contours of the structure. This will ultimately result in a cultured dermal tissue that mimics the anatomical features of real dermal tissue to a large extent.

It now has been discovered that if the concentration and effective volume of the polymeric solution used in processes of the present invention is selected appropriately and the process for preparing the foams includes a selected and carefully controlled quenching step prior to primary drying, foams having physicochemical properties suitable for use as tissue scaffolds in the repair and regeneration of dermal tissue, e.g. porosity and thickness, may be prepared. Such foams will have thickness of from about 0.25 mm to about 0.75 mm, preferably from about 0.4 mm to about 0.6 mm, and porosities of 90% or greater.

As indicated, critical steps involved in the preparation of these foams includes preparing a homogeneous polymer solution at a concentration suitable for preparing foam scaffolds having physicochemical properties suitable for use in repair and regeneration of dermal tissue. If the concentration of polymer is too high, foam porosity will be lower than what is useful in dermal tissue repair. Further, at higher solution concentrations, less shrinkage occurs during the quenching step, resulting in greater thickness for a given volume of solution. For polymers used in the present invention, a concentration of about 5% by weight polymer has been found particularly suitable for preparing preferred foam scaffolds useful in dermal tissue repair and regeneration. When such solutions are employed in lyophilization processes employing a quench cycle prior to drying, as claimed herein, foams of about 0.5 mm and which have porosity sufficient to function as a scaffold for dermal tissue repair and regeneration are provided. The volume of polymer solution utilized in preparing the foams will be effective to provide foams having thickness and porosity suitable for use as scaffolds in dermal tissue repair, as discussed herein. The volume to be employed for a particular foam scaffold will depend generally on the size, design and geometry of the particular mold used to prepare the foam scaffold. One skilled in the art will be able to determine readily the effective volume required for a particular application once having the benefit of this disclosure.

After selection of the appropriate solution concentration and effective volume, and prior to freezing and drying the polymer solution, the solution is subjected to a quenching step. As indicated above, inclusion of the quench step, in combination with proper selection of polymer concentration in the solution, is critical to forming foams having appropriate thickness and porosity for use in dermal tissue repair and regeneration. The temperature to which the solution is exposed for quenching must be less than the freezing temperature of the solution. The process according to the present invention requires an effective quenching rate, e.g. cooling rate, in the range of about 2° C./min to about 50° C./min, more preferably between about 4° C./min to about 20° C./min. In order to overcome the limitations of the relatively slower cooling rates of the commercial freeze dryers, in certain embodiments of the invention, the polymer solution contained in a mold is placed on a pre-cooled shelf. Depending upon the starting temperature of the solution, the temperature of the pre-cooled shelf and the heat transfer characteristics of the system, an effective quenching rate as noted above is obtained.

After quenching, the polymer solution is solidified, preferably by subjecting the solution to a freezing cycle. The frozen solution then is subjected to a vacuum drying cycle, as described more completely herein below. The freezing step phase separates the polymer solution and the vacuum drying step removes the solvent by sublimation and/or drying leaving a porous polymer structure or an interconnected open cell porous foam.

The polymer solution in a mold undergoes directional cooling through the wall of the mold that is in contact with the freeze dryer shelf, which is subjected to a thermal cycle. The mold and its surface can be made from virtually any material that does not interfere with the polymer-solvent system, though it is preferred to have a highly conducting material. The heat transfer front moves upwards from the lyophilizer shelf through the mold wall into the polymer solution. The instant the temperature of the mixture goes below the freezing point, the mixture also phase separates.

The morphology of this phase-separated system is locked in place during the freezing step of the lyophilization process and the creation of the open pores is initiated by the-onset of vacuum drying, resulting in the sublimation of the solvent. However, the mixture in the container or mold that is cooled from a heat sink will solidify prior to completely freezing. Although the mixture may appear solid, initially there appears to be some residual solvent associated with the polymer that has not crystallized. It is theorized, but in no way limiting the present invention, that a freezing front moves through the mixture from the heat sink to complete the solidification after the mixture has apparently solidified. The material in front of the freezing front at a given time will not be as cold as the material behind the front and will not be in a completely frozen state.

The pore size can be varied from a small pore size generally between about 10 microns and about 60 microns to a larger size of from about 60 microns to about 200 microns. Again this results from pulling a vacuum on the apparently solidified solution before it is completely solidified. The polymer concentration in the solution and the cooling rates are also important parameters in controlling the cell size. Ideally, the foam structure could be created to serve as a template to restore human dermal tissue.

Foams also can have channels. The channels formed by this process may traverse the thickness of the foam and generally range in diameter from about 30 to about 200 microns in diameter. The length of the channel generally is at least two times the channel's average diameter and, preferably, are at least four times the channel's average diameter and, most preferably, are at least eight times the channel's average diameter. The channel length and diameter will be selected based on the desired functionality of the channel, such as cell invasion, nutrient diffusion or as an avenue for vascularization.

The following examples are illustrative of the principles and practice of this invention, although not limited thereto. Numerous additional embodiments within the scope and spirit of the invention will become apparent to those skilled in the art.

EXAMPLES

In the examples which follow, the polymers and monomers were characterized for chemical composition and purity (NMR, FT-IR), thermal analysis (DSC), molecular weight (inherent viscosity), and baseline and in vitro mechanical properties (Instron stress/strain).

$^1$H NMR was performed on a 300 MHz NMR using $CDCl_3$ or HFAD as a solvent. Thermal analysis of segmented polymers and monomers was performed on a Dupont 912 Differential Scanning Calorimeter (DSC). A Fisher-Johns melting point apparatus was also utilized to determine melting points of monomers. Inherent viscosities (I.V., dL/g) of the segmented polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Example 1
Synthesis of a Random Poly($\epsilon$-caprolactone-co-glycolide)

A random copolymer of $\epsilon$-caprolactone-glycolide with a 35/65 molar composition was synthesized by ring opening polymerization reaction. The method of synthesis was essentially the method described in U.S. Pat. No. 5,468,253 in Example 6 (which is hereby incorporated herein by reference). The amount of diethylene glycol initiator added was adjusted to 1.15 mmole/mole of monomer to obtain the following characteristics of the dried polymer: The inherent viscosity (I.V.) of the copolymer was 1.59 dL/g in hexafluoroisopropanol at 25° C. The molar ratio of PCL/PGA was found to be 35.5/64.5 by proton NMR with about 0.5% residual monomer. The glass transition (Tg) and the melting points (Tm) of the copolymer were found to be −1° C., 1° C., 60° C. and 126° C. respectively, by DSC.

Example 2
Preparation of Porous Scaffolding for Skin Tissue Repair and Regeneration A 5% (wt./wt.) solution of the poly($\epsilon$-caprolactone-co-glycolide) described in Example 1 in 1,4-dioxane was prepared by dissolving 1 part by weight of the polymer to every 19 parts per weight of the solvent. The solution was prepared in a flask with a magnetic stir bar. For the copolymer to dissolve completely, it was gently heated to 60±5° C. and continuously stirred for a minimum of 4 hours but not exceeding 8 hours. Trace amounts of the polymer remained undissolved even after 8 hours of stirring. A clear homogeneous solution of the copolymer in 1,4-dioxane then was obtained by filtering the solution through an extra coarse porosity filter (Kimble, Kimax Buchner funnel with Kimflow fritted disc) using dry nitrogen to help in the filtration of this viscous solution.

An effective volume of the polymer solution was poured into an aluminum mold of internal dimensions 11.4 cm×11.4 cm×1.27 cm height. The mold thickness itself was 0.125 cm. A scaffold sheet approximately 0.5 mm thick was prepared as follows.

The mold dish with the solution was placed carefully (without tilting) on a pre-cooled shelf of an FTS Dura Dry Freeze dryer. The pre-cooled shelf was maintained at about −17° C. for about 15 minutes prior to quenching the polymer solution. The cycle was started and the shelf temperature was held at −17° C. for 60 minutes to complete freezing. After 60 minutes of freezing at −17° C., a vacuum was applied to initiate primary drying of the dioxane by sublimation and held at 100 mTorr for one hour. Next, secondary drying was conducted at 5° C. for one hour and at 20° C. for one hour. At each temperature the vacuum level was maintained at 20 mTorr.

At the end of the second stage, the lyophilizer was brought to room temperature and the vacuum was broken with nitrogen. The chamber was purged with dry nitrogen for approximately 30 minutes before opening the door. The foams then were removed from the molds by simply lifting off the surface. The foams then were packaged and sterilized by well known techniques, such as ethylene oxide sterilization or gamma irradiation, to make the scaffolds sterile and ready to be used as a biomedical implant.

Figure 1B:
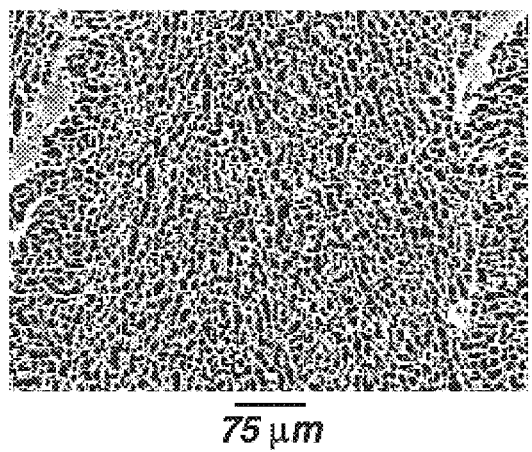
FIG. 1b is a scanning electron micrograph of the bottom surface of a foam scaffold according to the present invention.
Figure 1C:
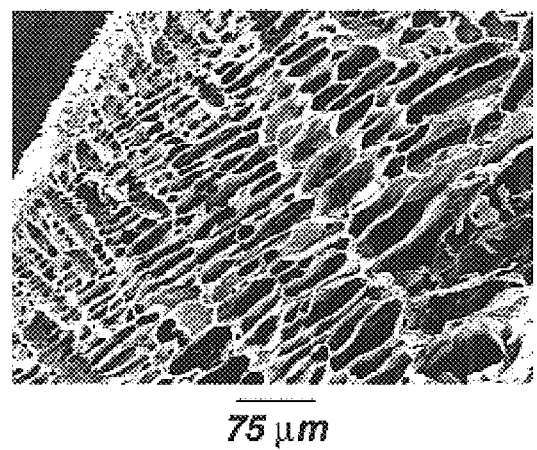
FIG. 1c is a scanning electron micrograph of a cross section of a foam scaffold according to the present invention.

The foam prepared by this process is exemplified in FIGS 1a, 1b and 1c. Foams prepared accordingly were determined to be about 0.5 mm thick and had porosity of 93% as determined by Helium Pycnometry, per ASTM standard test method D6226, "Open cell contents of rigid cellular plastics". In vivo studies were conducted and such foams were completely absorbed by the body within about 90 to 120 days.

A comparative foam was prepared utilizing a polymer solution comprising 10% by weight of the 35/65 (PCL/PGA) copolymer and a modified lyophilization process employing a slower, controlled cooling cycle (about 0.5° C./min) rather than a quench step as per the present invention. The volume of solution used was adjusted to provide a foam thickness of about 0.5 mm. Such foams had a porosity of 87.1% and were 0.5 mm thick. Such foams were determined to be sub-optimal for repair and regeneration of dermal tissue and exhibited poor tissue ingrowth when tested in a porcine in vivo model.

A second comparative foam was prepared utilizing a polymer solution comprising 10% by weight of a 40/60 (PCL/PLA) copolymer and a modified lyophilization process employing a slower, controlled cooling cycle (about 0.5° C./min) rather than a quench step per the present invention. Such foams were about 2 mm thick and had porosity of about 80%. Such foams were determined to be sub-optimal for repair and regeneration of dermal tissue and exhibited poor tissue ingrowth. In addition, such foams were not absorbed by the body until about 18 months after implantation.

Figure 2A:
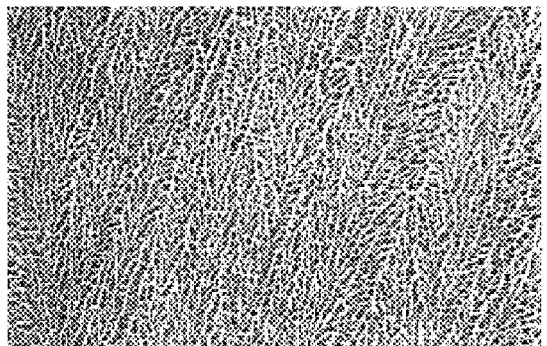
FIG. 2a is a scanning electron micrograph of the top surface of a comparative foam scaffold.
Figure 2B:
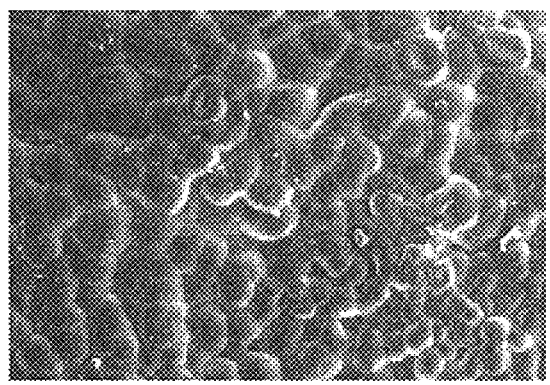
FIG. 2b is a scanning electron micrograph of the bottom surface of a comparative foam scaffold.
Figure 2C:
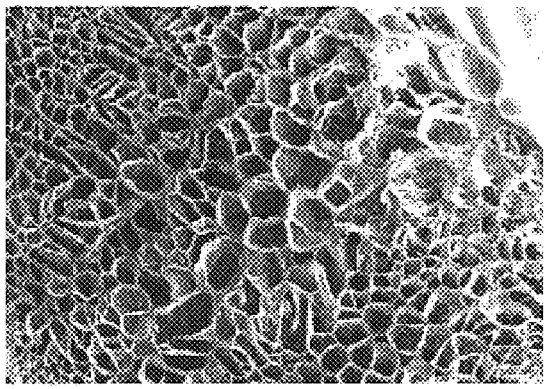
FIG. 2c is a scanning electron micrograph of a cross section of a comparative foam scaffold.

A third comparative foam scaffold was prepared utilizing a 35:65 (PCL/PGA) polymer solution and a slow cool cycle. The resultant foam had a thickness of 2 mm and porosity of about 80%. The foam is depicted in FIGS. 2a–2c.

Example 3
Human Clinical Trial to Evaluate the Porous Scaffolding for Dermal Tissue Repair and Regeneration This example describes the clinical trial to evaluate the performance of porous scaffolds (implants) in venous stasis ulcers. These are chronic wounds that are difficult to heal. The concept is to implant the bioabsorbable porous foam tissue scaffold of the present invention in the wound bed, thereby providing a provisional matrix that will aid in the formation of granulation tissue, which in turn subsequently will aid in re-epithelialization and wound closure. In other words this provisional matrix aids in the repair and regeneration of the dermal and epidermal tissues. Patients who have venous stasis ulcers are finally selected based on their clinical history, the underlying pathological conditions and some contra-indications. The objective of this pilot clinical study is to evaluate the patient's acceptance of the implant in terms of how the implant is incorporated in the wound bed at 2 weeks. Secondly, the study also monitors how the wound heals over a 12-week period and evaluates wound closure.

The foam scaffold implants, which come in the form of porous sheets, are 10 cm×10 cm×0.5 mm thick. These are first prepared using the method described in Example 2. The product is sterilized using standard ethylene oxide cycle. Before placing the implant on the patient's wound bed, the patient's wound bed is debrided either surgically or non-surgically. Non-surgical debridement could include autolytic, enzymatic or biological debridement.

Once the wound bed is debrideded and cleaned it is ready for the implant. The porous scaffold is taken from the pack and cut to fit the wound using scissors. The product is soaked in saline immediately prior to application to encourage fit to the wound bed. Once the foam scaffold implant is applied to the wound bed, the wound bed is covered with a non-adherent secondary dressing. Appropriate other secondary dressings may be used as needed for compression therapy.

The foam scaffold preferably will be enveloped by granulation tissue and absorbed by the body within about 90 days of implantation.

We claim:

1. A synthetic, biocompatible, bioabsorbable foam scaffold suitable for use in the repair and/or regeneration of dermal tissue in a body of a patient: comprising, a synthetic, biocompatible, bioabsorbable, aliphatic, elastomeric copolymer comprising copolymerized $\epsilon$-caprolactone and glycolide at a molar ratio of $\epsilon$-caprolactone:glycolide ranging from about 30:70 to about 40:60, wherein said scaffold is about 0.25 mm to about 0.75 mm thick and has porosity of 90 percent or greater.

2. The foam scaffold of claim 1 wherein said foam scaffold is about 0.4 mm to about 0.6 mm thick and has porosity from 90 percent to 97 percent.

3. The foam scaffold of claim 1 wherein the copolymer comprises about 35 mole percent $\epsilon$-caprolactone copolymerized with about 65 mole percent glycolide.

4. The foam scaffold of claim 3 wherein the scaffold is about 0.5 mm thick and has porosity of about 93 percent.

5. The foam scaffold of claim 1 wherein said scaffold is adapted to be substantially absorbed by the body within about 120 days of implantion.

6. The foam scaffold of claim 1 wherein said foam scaffold is adapted to be completely absorbed by the body within about 90 days of implantion.

7. The foam scaffold of claim 1 wherein about 50 percent of said thickness of said foam scaffold is adapted to be infiltrated by granulation tissue within about 10 days of implantation.

8. The foam scaffold of claim 1 wherein about 75 percent of said thickness of said foam scaffold is adapted to be infiltrated by granulation tissue within about 7 days of implantation.

9. The foam scaffold of claim 1 wherein said foam scaffold is adapted to be substantially submerged in or enveloped by granulation tissue within about 28 days of implantation.

10. The foam scaffold of claim 1 wherein said foam scaffold is adapted to be completely submerged in or enveloped by granulation tissue within about 28 days of implantation.

* * * * *